United States Patent [19]

Farzin-Nia

[11] Patent Number: 5,588,832
[45] Date of Patent: Dec. 31, 1996

[54] METHOD OF FABRICATING METAL INSTRUMENTS FROM RAW MATERIAL AND ORTHODONTIC PLIERS MADE THEREBY

[75] Inventor: Farrokh Farzin-Nia, Inglewood, Calif.

[73] Assignee: Ormco Corporation, Glendora, Calif.

[21] Appl. No.: 294,653

[22] Filed: Aug. 23, 1994

[51] Int. Cl.[6] .................. A61C 3/00; B21D 28/00; B25B 7/02; B21K 5/00
[52] U.S. Cl. .................. 433/4; 76/119; 72/339; 81/415
[58] Field of Search .................. 76/101.1, 104.1, 76/105, 106.5, 119; 59/61, 62; 433/8, 4; 72/337, 339; 81/415; 29/434

[56] References Cited

U.S. PATENT DOCUMENTS

| | | | |
|---|---|---|---|
| 1,990,694 | 2/1935 | Jacobs | 76/104.1 X |
| 2,045,025 | 6/1936 | Richardson | 433/8 X |
| 2,825,248 | 3/1958 | Ahlbin | 76/106.5 |
| 2,852,963 | 9/1958 | Lyon, Jr. | 76/105 X |
| 3,600,979 | 8/1971 | Rozmus | 76/101.1 |
| 3,774,306 | 11/1973 | Dobyne | 433/4 |
| 5,066,225 | 11/1991 | Jones et al. | 433/8 |
| 5,328,361 | 7/1994 | Ezcurra | 433/4 |

*Primary Examiner*—Robert P. Swiatek
*Assistant Examiner*—Yvonne R. Abbott
*Attorney, Agent, or Firm*—Wood, Herron & Evans, P.L.L.

[57] ABSTRACT

Corrosion resistant instruments such as those used in medicine and dentistry are efficiently made from raw materials that are difficult to machine. Round bar stock is rolled or otherwise deformed to have flat sides and rounded edges. The parts of the instrument are cut from the flattened bar, by combinations of transverse and longitudinal cuts, so that the rounded edges of the bar define the shape of convexly curved finish surfaces of the instrument. Expensive machining steps are eliminated. An orthodontic pliers is particularly disclosed, made according to the method, by making one or more Z-shaped cuts that preserve the rounded sides to define the outer surfaces of a handle and opposing jaw on each of two plier parts, pivotally joined together.

21 Claims, 1 Drawing Sheet

U.S. Patent  Dec. 31, 1996  5,588,832
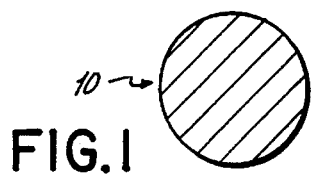
FIG.1
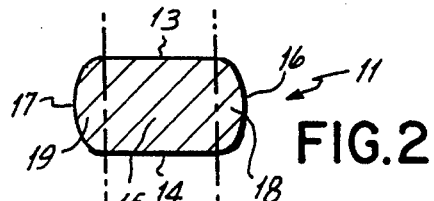
FIG.2
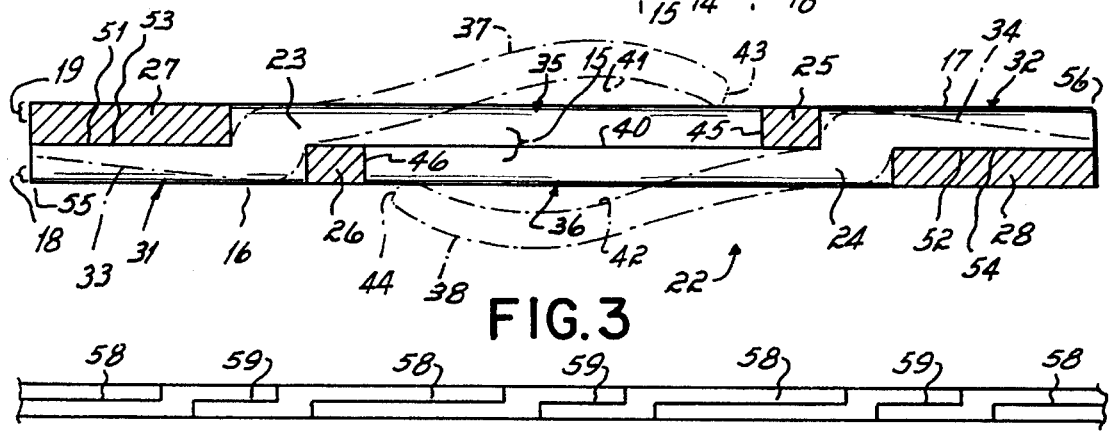
FIG.3
FIG.3A
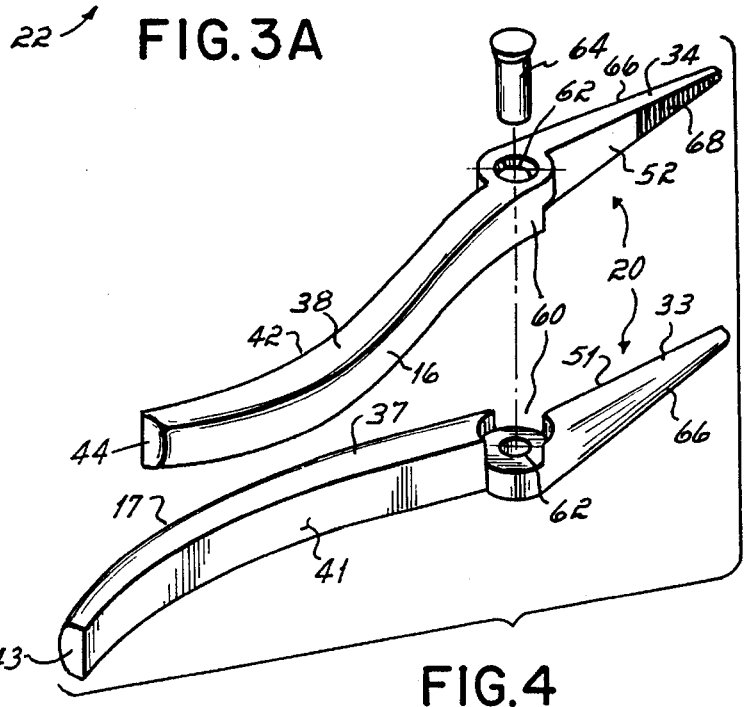
FIG.4
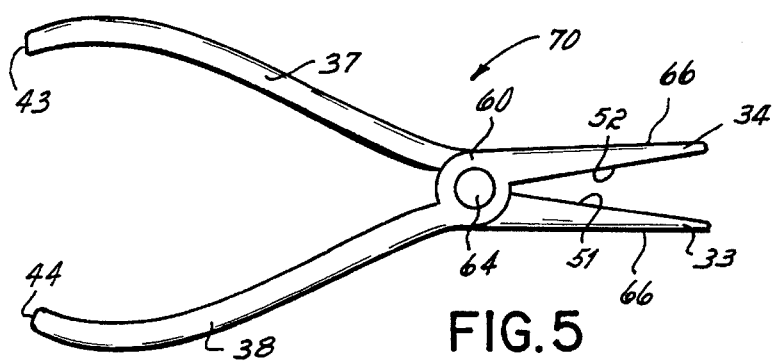
FIG.5

METHOD OF FABRICATING METAL INSTRUMENTS FROM RAW MATERIAL AND ORTHODONTIC PLIERS MADE THEREBY

The present invention relates to the manufacture of instruments, particularly hand held medical and dental instruments such as those used in orthodontics, particularly instruments on which rounded surfaces are desired for user comfort. More particularly, the present invention relates to a method of fabricating such instruments from raw material, especially difficult-to-machine hard, corrosion resistant metals such as stainless steel and titanium alloys.

BACKGROUND OF THE INVENTION

Medical instruments, instruments used in orthodontics, and instruments for several other fields, particularly hand held instruments, must often be made of strong corrosion resistant metals such as titanium, titanium alloys, or stainless steel. Such materials are frequently difficult to machine and therefore present problems in the fabrication of the instrument parts from the raw material stock. Because hand held instruments used in medicine and dentistry require a combination of flat and curved surfaces, the instrument manufacturing processes of the past have required the performance of combinations of cutting, milling and grinding steps on the hard raw material, contributing substantially to the cost of the manufacture of such instruments of such materials compared to the manufacture of similar tools of other steels and materials.

Hand held instruments such as cutters and pliers require the application of at least moderate force by the user. For example, in orthodontics, orthodontic pliers used in the bending of archwires and the manipulation of other parts of orthodontic appliances require not only a delicate use of the plier instrument, but the exertion of considerable force from the user's hand. Thus, the manufacture of such instruments with rounded handles has been regarded as necessary to allow orthodontists to use such instruments effectively and with comfort. Because such instruments must be resistant to contamination and are subjected to high sterilization temperatures, the bonding of more easily shaped organic materials to the handles and other parts of the instrument is not desirable.

Typically, a stainless steel tool, such as a pair of pliers, is made from a block or bar stock of raw material of rectangular cross-section. The components of the instruments, in the case of pliers, include two nearly identical parts cut from the stock raw material. The cut parts are then shaped and machined into the components of the instrument. The handle portion of such an instrument, and other outside surfaces, are then rounded by a process such as grinding, to remove the 90° corners where the tool contacts the users hand. The rounding process leaves a curved contour that can be gripped with considerable force without subjecting the user to discomfort or interfering with the use of the tool. The curved surfaces are also provided on the parts of the tool that contact the patient, for the comfort of the patient and to protect the patient from injury. Such grinding and other machining process required to impart the curved outer surfaces to instruments made of such difficult to machine materials substantially adds to the increased cost of instruments made of such metals.

Accordingly, there is a need for a better and less costly method of fabricating instruments out of metals and other materials that are difficult to machine where curvature of certain surfaces of the finished instrument is desired.

SUMMARY OF THE INVENTION

A primary objective of the present invention is to provide a method for manufacturing instruments out of hard-to-machine materials where the fabrication of curved surfaces are desirable. A particular objective of the present invention is to provide an economical method of fabricating curved surfaces on handles and other portions of hand held instruments where otherwise sharp corners present a hazard, discomfort or inconvenience to the user, to a patient of the user, or to equipment or other items which the instrument might contact.

It is a more particular objective of the present invention to provide an instrument manufacturing method that eliminates or reduces steps in the fabrication of hard metal raw material such as the grinding, milling or cutting of curved surfaces to remove the sharp corners of the product.

According to the principles of the present invention, there is provided a method by which instruments can be manufactured out of hard-to-machine metal without the use of additional machining steps to form curved surfaces in handles and the like. The method utilizes round bar stock or rods, rather than bars of rectangular cross section, to form the parts. The round bars are rolled and thereby partially flattened, leaving two parallel flat surfaces with rounded, generally semicircular, sides.

In accordance with the preferred embodiment of the invention, two plier or cutter halves are cut from the partially flattened round bars by arrangement of the patterns for the parts such that the curved sides of the bars coincide with the curved surfaces that are desired in the instrument. The parts are then shaped and machined to the degree necessary to satisfy other functional and dimensional requirements of the instrument, leaving the original curved surfaces to form the surfaces of the handles or the other curved surfaces required.

In the specifically illustrated and described embodiment of the invention, a method of fabricating surgical or orthodontic pliers is provided, in which the principles of the invention are particularly advantageous. In this application of the invention, round bar stock is rolled to provide a semi-flattened bar of oblong cross-section in which the curved side surfaces will form the curved handle portion of the pliers and also the curved backs of the plier jaws. Two nearly identical halves are formed into the two scissor parts of the plier, each including a handle for one side of the pliers along with the jaw of the opposite side. Therefore, it is only necessary to machine the jaw surface, arcuately form the handles appropriately, then construct a pivot pin and assembling the parts. No grinding, cutting or other machining is required to form most of the rounded surfaces of the handles and jaws.

With the present invention, considerable cost is eliminated from the instrument manufacturing process by eliminating the rounding steps. Several dollars per part, which represents a substantial percentage of the manufacturing cost, is saved.

These and other objectives and advantages of the present invention will be more readily apparent from the following detailed description of the drawings and preferred embodiments, in which:

BRIEF DESCRIPTION OF THE DRAWINGS

FIG. 1 is a cross-sectional view of a piece of round bar stock suitable for use with the present invention.

FIG. 2 is an end view of the bar stock of FIG. 1 after being deformed in the course of the practice of the present invention.

FIG. 3 is a plan view of the deformed bar stock of FIG. 2 illustrating the cutting of instrument parts therefrom in accordance with one embodiment of the present invention.

FIG. 3A is a plan view, similar to FIG. 3, illustrating the cutting of instrument parts from the deformed bar stock of FIG. 2 in accordance with an alternative embodiment of the present invention.

FIG. 4 is an exploded perspective view of the assembly of the parts of FIGS. 3 or 3A for the formation of orthodontic pliers according to the present invention.

FIG. 5 is a top view illustrating the parts of FIG. 4 fully assembled into a pliers.

DETAILED DESCRIPTION OF THE PREFERRED EMBODIMENTS

The manufacture of an instrument according to the principles of the present invention is illustrated for a pair of pliers particularly suited for use in the orthodontic treatment of patients. The method of forming the instrument, according to the preferred embodiment of the present invention, is preferably begun with an elongated piece of stock material of which the instrument is to be formed. Such a material is, for example, corrosion resistant metal such as nickel-titanium alloys, stainless steel, or other generally metallic material. Such materials are particularly difficult to machine, particularly by grinding or otherwise reshaping of their surfaces. A piece of bar stock 10 of such a material in the form of a rod having a generally round cross-section is illustrated in FIG. 1.

The fabrication of instrument parts, according to the preferred embodiment of the method of the present invention involves the deformation of the round bar 10, preferably compressively, such as by rolling, stamping, or other operation, to produce a bar 11 of the elongated cross-section illustrated in FIG. 2. The bar 11, thus deformed, has generally parallel top and bottom surfaces 13 and 14, respectively, defining a generally central region 15 of the bar 11, and opposite right and left rounded side surfaces 16 and 17, respectively, defining right and left edge regions 18 and 19.

From the bar 11, thus deformed, pieces of the material are cut to form parts 20 of the instrument 70 (FIG. 5). In FIGS. 3 and 3A, a plurality of part blanks for formation of a pair of pliers 70 suitable for medical or dental use are illustrated. Preferably, for such an instrument, a plurality of the part blanks, two of which are required for each pair of pliers, are illustrated. In the version of FIG. 3 two such part blanks 23 and 24 are laid out on a relatively short piece of the deformed bar 11 for the manufacture of a single pair of the pliers 70. In the embodiment of FIG. 3A, a plurality of similar part blanks 22 is laid out for cutting from a longer piece of the deformed bar 11. In the embodiment of FIG. 3, the part blanks 23 and 24 are laid out for cutting by mechanical methods such as by band saw cutting or other form of cutting with a blade of a predetermined width. Such a layout results in cutouts 25–28 that are scrapped and recycled. In the embodiment of FIG. 3A, the plurality of part blanks 22 is laid out to more fully use the material, which may be cut by use of electric discharge machining (EDM), laser cutting, or other technique which is currently available or may hereafter be developed.

The cutting of the part blanks 23 and 24 from the bar 11 is described in detail with reference to FIG. 3, which illustrates each of the part blanks 23 and 24 with a head or jaw section 31,32, respectively, from which the jaws 33,34 of a pliers are to be formed, and a handle portion 35, 36, respectively, from which the handles 37,38 of the pliers are to be formed. The jaws 33,34 and handles 37,38 are illustrated in phantom in FIG. 3.

The cutting of the part blanks 23,24 from the deformed bar 11 preferably proceeds by separating the two pieces primarily by a longitudinal cut 40 in the center portion 15 of the bar, cutting through from the top surface 13 to the bottom surface 14 in a straight vertical line that represents the cutting edge of a cutting tool (not shown). The cut 40, is normally a vertical plane represented by a line in FIG. 3, defined by the horizontal path of the cutting edge as it is translated longitudinally along the deformed bar 11, preferably approximately along the longitudinal centerline of the bar 11.

This cut 40 extends along a major portion of the length of the part blanks 23,24 and preferably defines the approximate shape of the finish surfaces of the inner sides 41,42, respectively, of handles 37,38 formed from handle portions 35,36 of the blanks 23,24, respectively. Additionally, heels 43,44, respectively of the handles 37,38 are preferably formed by transverse cuts 45,46 extending from the rounded side surfaces 16,17, respectively, to the central portion 15 of the bar 11 through the side portions 18,19, respectively. The transverse cuts may include multiple cuts to remove the pieces 25, 26 and allow for manipulation of the cutting tool, where required by the cutting process selected. This procedure leaves the original rounded side surfaces 16,17 of the bar 11 to define the approximate finish shape of the convex outer surfaces 57, 58 of the handles 37,38, respectively. While these surfaces may be subjected to a subsequent finishing process, the rounded convex cross-sectional shape is generally retained, avoiding the necessity of grinding or otherwise shaping the surfaces 57 and 58 of handles 38 and 37 to impart a curvature.

The head sections 31,32 may also, in the process described above, be formed into plier jaws 33,34, respectively, that utilize at least a portion of the curved outer side surfaces 17, 16 of the bar 11 to define convex outer surfaces of the instrument. In such an embodiment, the rounded side surface 17 defines the convex outer surface of the handle 37 of part blank 23 and a portion of the outer convex surface 57 of the head section 32 of the other part blank 24. Similarly, the rounded side surface 16 defines the convex outer surface of the handle 38 of part blank 24 and a portion of the convex outer surface of the head section 31 of the part blank 23.

Additionally, gripping surfaces 51, 52 are defined for the jaws 33,34 by cuts 53,54. Such cuts 53,54 may be formed longitudinally from an end 55 or 56 of the bar 11 and transversely to one of the side surfaces 17 or 16 (e.g., in the embodiment of FIG. 3), or may be a Z-shaped cut 59, similar to alternating cuts 58 that are longer in the longitudinal direction, that separates the different part blanks 22. The alternating long and short Z-shaped cuts 58 and 59 are illustrated in connection with the embodiment of FIG. 3A, with the longer cuts 58 separating the handle portions 35,36 of adjacent blanks 22, and the shorter cuts 59 separating the head sections 31,32 of the blanks 22.

Following formation of the part blanks 22 as described above, the parts 20 are formed. To complete this formation, the handles 37,38 are bent into shape, for example by a stamping process, and machining of the jaws 33,34 is carried out, such as by a grinding or cutting process, to impart a tapered surfaces 66 to the jaws and to add serrations 68.

Additionally, an intermediate portion 60 of each part 20 is machined or otherwise formed into a hinge 62, as illustrated in FIG. 4, at which the parts 20 are pivotally interconnected by a pin 64 to form the assembled pliers 70, as illustrated in FIG. 5. Alternatively, instead of forming a plier-type instrument, a cutter-type instrument may be formed by machining surfaces forming of the jaws 33,34 of each part to form an inwardly facing cutting edge and pivotally interconnecting the parts between the cutting edge and handle of each so that these surfaces can be pivoted into mutual contact, thereby forming a cutter-type instrument.

The process described above is suitable for the manufacture of other instruments, particularly from hard, corrosion resistant materials that are difficult to machine into curve surfaces following the cutting of parts from traditional stock pieces of rectangular cross-section. Instruments, particularly hand held medical and dental instruments of one or more parts are particularly advantageously manufactured by the process of the present invention.

From the description above, it will be apparent to those skilled in the art that various additions and modifications can be without departing from the principles of the present invention.

Therefore, I claim:

1. A method of fabricating an instrument having a handle and a head each formed of a portion of two pivotally interconnected parts each having a convexly curved surface thereon, the method comprising the steps of:

providing a bar of raw metallic material having an elongated cross-section, generally flat parallel top and bottom surfaces and two opposite convex side surfaces;

separating the bar into two pieces by a cut through the bar to at least partially form a part from each of the pieces, each part having two ends and an outer surface of a convex shape defined by a convex side surface of the bar;

manufacturing from the parts an instrument having at least two outer surfaces having the convex shape;

forming a handle portion at one end of each of the parts that includes the outer surface thereof of the convex shape, and forming a head portion at the other end of each of the parts; and pivotally interconnecting the parts between the handle portion and head portion to form an instrument having a handle and a head such that the force can be applied against the convex shape of the outer surfaces of the parts to pivot the head portions toward each other.

2. The method of claim 1 wherein:

the bar providing step includes the step of deforming a bar of raw metallic material having a nominally round cross section into the bar of elongated cross-section having the generally flat parallel top and bottom surfaces and the two convex side surfaces of the bar.

3. The method of claim 1 wherein:

the separating step includes the step of cutting the bar into the two pieces such that each piece forms one of the parts, each part having one side defined by the cut and having at least one outer side of a convex shape defined each by a different one of the two convex side surfaces of the bar.

4. The method of claim 3 wherein:

the separating step includes the step of cutting the bar through from the top surface to the bottom surface along a path at least partially extending longitudinally along the bar.

5. An instrument manufactured in accordance with the method of claim 4.

6. An instrument manufactured in accordance with the method of claim 1.

7. A method of fabricating an instrument having convexly curved surfaces, the method comprising the steps of:

providing a bar of raw metallic material having an elongated cross-section, generally flat parallel top and bottom surfaces and two opposite convex side surfaces;

separating the bar into two pieces by a cut through the bar to at least partially form a part from each of the pieces, each part having an outer surface of a convex shape defined by the convex side surfaces of the bar; and manufacturing from the parts an instrument having at least two outer surfaces having the convex shape;

the separating step further comprising the steps of:

further cutting the bar along two additional cuts such that each defines an additional surface on each of the parts; and the cutting steps being performed to separate from the bar each of the parts such that each part has two outer surfaces of a convex shape each defined by a different one of the convex side surfaces of the bar, and such that each part has at least one surface defined by each of the cuts.

8. The method of claim 7 wherein:

the separating step includes the step of forming each of the parts to substantially identical shapes.

9. The method of claim 8 further comprising the steps of:

bending each of the separated parts to form a curved handle having a convex outer surface having the convex shape, and a flat inner side;

machining the additional surfaces of each part that is defined by the additional cut to form an inwardly facing gripping jaw on each part; and pivotally interconnecting the parts between the gripping jaw and handle of each so that the machined surfaces can be pivoted toward each other, thereby forming a plier-type instrument.

10. A plier-type instrument manufactured in accordance with the method of claim 9.

11. The method of claim 8 wherein:

bending each of the separated parts to form a curved handle having a convex outer surface having the convex shape, and a flat inner side;

machining at least one of the additional surfaces of at least one part that is defined by the additional cut to form an inwardly facing cutting edge; and pivotally interconnecting the parts between the cutting edge and handle of each so that the additional surfaces can be pivoted toward each other, thereby forming a cutter-type instrument.

12. A cutter-type instrument manufactured in accordance with the method of claim 11.

13. A method of forming pliers of hard corrosion resistant metal, the method comprising the steps of:

providing a bar of hard corrosion resistant metallic material having an elongated cross-section with generally flat parallel top and bottom surfaces defining a longitudinal center portion and two rounded side surfaces each defining an edge portion, the bar having two ends;

cutting the bar through and thereby separating two parts therefrom, one part including at least some of one edge portion and at least some of one end and the other part including at least some of the other edge portion and at least some of the other end;

fabricating the ends into a pair of plier jaws, one on each of the parts, and fabricating the edge portions of the respective parts into a pair of plier handles, one on each of the parts, to form a pair of plier halves having convex outer surfaces having a cross-sectional shape generally defined by the rounded side surfaces of the bar; and forming each of the parts between the handle and jaw thereof into a hinge pivotally joining the parts thereat together.

14. The method of claim 13 wherein:

longitudinally rolling a bar of a hard corrosion resistant metallic material from a nominally round cross-section to compressively deform the bar to the elongated cross-section having the generally flat top and bottom surfaces and the two rounded side surfaces.

15. An orthodontic pliers manufactured in accordance with the method of claim 13.

16. The method of claim 13 wherein:

the cutting step includes the step of cutting the bar transversely from one of the rounded side surfaces through the one of the edge portions to the center portion, longitudinally along the center portion, and transversely from the center portion through the other edge portion to the other rounded side surface; and the fabricating step includes the step of forming the jaws and handles on each of the parts such that:
  each part includes a handle having an outer convex surface having a cross-sectional shape generally defined by the one of the side surfaces of the bar and a jaw having a concave outer surface having a cross-sectional shape generally defined by the other side surface of the bar, and
  the handle of one part has the convex outer surface thereof having a cross-sectional shape generally defined by the one side surface of the bar while the handle of the other part has a convex outer surface having a cross-sectional shape generally defined by the other side surface of the bar.

17. An orthodontic plier or cutter type instrument manufactured according to the method comprising the steps of:

providing a bar of a hard corrosion resistant metallic material having an elongated cross-section with generally flat top and bottom side surfaces defining a longitudinal center portion and two rounded side surfaces of an original uncut and unmachined curvature defining two edge portions, the bar having two ends;

cutting the bar and thereby separating two parts therefrom, one part including at least some of one edge portion and at least some of one end and the other part including the at least some of the other edge portion and at least some of the other end;

fabricating the ends into a pair of jaws, one on each of the parts, and fabricating the edge portions into a pair of handles, one on each of the parts, to form a pair of instrument halves having convex outer hand-gripping surfaces each having a cross-sectional shape generally defined by the rounded side surfaces of the bar;

forming each of the parts between the handle and jaw thereof into a hinge and pivotally joining the parts together at the hinge thereof to form the instrument; and the cutting step including the step of cutting the bar transversely from one side surface through one edge portion to the center portion, longitudinally along the center portion, and transversely from the center portion through the other edge portion to the other side surface; and wherein the instrument that is formed by the method includes the two pivotally interconnected parts, with the handle of each part having its outer convex hand- gripping surface being one of the side surfaces of the bar that is of the original uncut and unmachined curvature.

18. The instrument of claim 17 wherein:

the fabricating step includes the step of forming the jaws and handles on each of the parts such that:
  each part a jaw having a convex outer surface having a cross-sectional shape generally defined by the other side surface of the bar, and
  the handle of one part has the convex outer surface thereof having a cross-sectional shape generally defined by the one side surface of the bar while the handle of the other part has a convex outer surface having a cross-sectional shape generally defined by the other side surface of the bar.

19. The instrument of claim 17 wherein:

the fabricating step includes the step of forming a clamping surface on each of the jaws to thereby manufacture a plier-type instrument.

20. The instrument of claim 17 wherein:

the fabricating step includes the step of forming a cutting surface on each of the jaws to thereby manufacture a cutter-type instrument.

21. The instrument of claim 17 wherein:

the fabricating step includes the step of sawing the bar to produce confronting clamping surface, one on each of the jaws, to thereby manufacture a plier-type instrument.

* * * * *